United States Patent [19]
Gacsályi et al.

[11] Patent Number: 6,093,747
[45] Date of Patent: Jul. 25, 2000

[54] 1,7,7-TRIMETHYL-BICYCLO[2.2.1]HEPTANE DERIVATIVES AS ANXIOLYTIC AGENTS HAVING ENHANCED RECEPTOR SPECIFICITY

[75] Inventors: István Gacsályi; Imre Klebovich; Zoltán Budai; Gyula Lukács; Erzsébet Kaufmanné Bojti; Éva Schmidt; István Gyertyan; András Bilkei Gorzó; Gábor Blaskó ; Miklos Abermann; Katalin Baloghne Nemes; Gyula Grézál; András Egyed, all of Budapest, Hungary

[73] Assignee: Egis Gyógyszergyár RT., Budapest, Hungary

[21] Appl. No.: 09/284,609

[22] PCT Filed: Oct. 16, 1997

[86] PCT No.: PCT/HU97/00064

§ 371 Date: Jun. 14, 1999

§ 102(e) Date: Jun. 14, 1999

[87] PCT Pub. No.: WO98/17230

PCT Pub. Date: Apr. 30, 1998

[30] Foreign Application Priority Data

Oct. 17, 1996 [HU] Hungary ............................. 96 02868

[51] Int. Cl.$^7$ .................................................. A01N 33/02
[52] U.S. Cl. ................................................................ 514/650
[58] Field of Search ............................................. 514/650

[56] References Cited

FOREIGN PATENT DOCUMENTS 2153083 1/1996 Canada .

*Primary Examiner*—Paul J. Killos
*Attorney, Agent, or Firm*—Smith Gambrell & Russell, LLP

[57] ABSTRACT

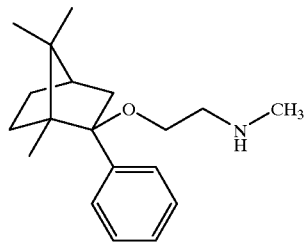

(I)

The new compound of Formula (I) and salts thereof possess valuable anxiolytic properties.

14 Claims, No Drawings

1,7,7-TRIMETHYL-BICYCLO[2.2.1]HEPTANE DERIVATIVES AS ANXIOLYTIC AGENTS HAVING ENHANCED RECEPTOR SPECIFICITY

TECHNICAL FIELD OF THE INVENTION

The present invention relates to new 1,7,7-trimethyl-bicyclo[2.2.1]heptane derivatives, a process for the preparation thereof and the use of said compounds as pharmaceutical active ingredient.

BACKGROUND OF THE INVENTION

It is known that (1R,2S,4R)-(−)-2-phenyl-2-dimethylaminoethoxy-1,7,7-trimethyl-bicyclo[2.2.1]heptane is a non-benzodiazepine type potential anxiolytic compound. The INN of (1R,2S,4R)-(−)-2-phenyl-2-dimethylaminoethoxy-1,7,7-trimethyl-bicyclo[2.2.1]heptane-hemifumarate is deramciclane (Hungarian patent No 179,164).

SUMMARY OF THE INVENTION

It is the object of the present invention to provide new 1,7,7-trimethyl-bicyclo[2.2.1]heptane derivatives which have a similar structure to that of (1R,2S,4R)-(−)-2-phenyl-2-dimethylaminoethoxy-1,7,7-trimethyl-bicyclo[2.2.1]heptane, but are different in their receptor profile, mechanism of action and anxiolytic animal test model.

The above object is reached by the new compounds of the present invention.

According to an aspect of the present invention there is provided the new compound of the Formula I and pharmaceutically acceptable acid addition salts thereof.

According to a further aspect of the present invention there is provided a process for the preparation of the new compound of the Formula

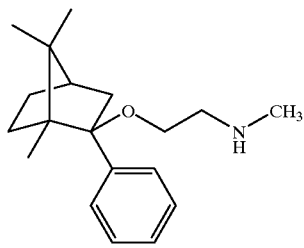

(I)

and pharmaceutically acceptable acid addition salts thereof.

According to a still further aspect of the present invention there are provided pharmaceutical compositions comprising as active ingredient the compound of the Formula I or pharmaceutically acceptable acid addition salts thereof.

According to a still further aspect of the present invention there is provided a process for the preparation of the above pharmaceutical compositions.

According to a still further aspect of the present invention there is provided the use of the compound of the Formula I and pharmaceutically acceptable acid additon salts thereof as active ingredient of pharmaceutical compositions, having particularly anxiolytic effect.

The compound of the Formula I and pharmaceutically acceptable acid addition salts thereof possess valuable anxiolytic properties.

The compound of the Formula I may be present in racemic or optically active form. The present invention encompasses both the racemic and the optically active forms.

According to a particularly preferable feature of the present invention there is provided (1R,2S,4R)-(−)-2-phenyl-2-methylaminoethoxy-1,7,7-trimethyl-bicyclo[2.2.1]heptane and pharmaceutically acceptable acid addition salts thereof.

DETAILED DESCRIPTION OF THE INVENTION

The compound of the Formula I and pharmaceutically acceptable acid addition salts may be used for anxiolytic treatment by administering to a patient in need of such treatment a pharmaceutically active amount of the compound of the Formula I or a pharmaceutically acceptable acid addition salt thereof. In said treatment it is preferred to use as active ingredient (1R,2S,4R)-(−)-2-phenyl-2-methylaminoethoxy-1,7,7-trimethyl-bicyclo[2.2.1]heptane and salts thereof.

The pharmaceutically acceptable acid addition salts of the compound of the Formula I may be salts formed with inorganic or organic acids. For salt formation e.g. hydrogen halides such as hydrochloric acid or hydrogen bromide; or sulphuric acid, nitric acid, phosphoric acid, acetic acid, propionic acid, malic acid, lactic acid, maleic acid, fumaric acid, tartaric acid, succinic acid, methanesulfonic acid, p-toluenesulfonic acid, etc. may be used. Salts formed with fumaric acid proved to be particularly advantageous.

According to the process of the present invention the compound of the Formula

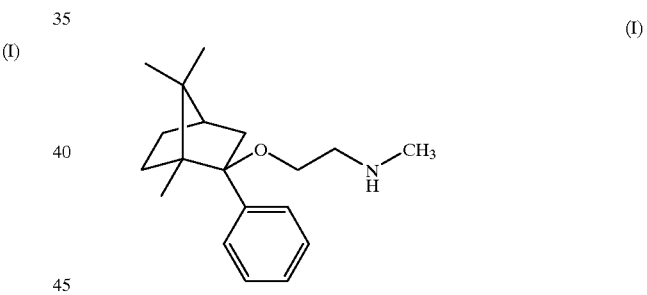

(I)

and pharmaceutically acceptable acid addition salts thereof may be prepared by a.) demethylating the compound of the Formula

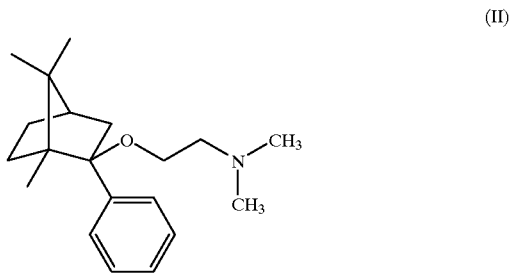

(II)

or b.) removing the protecting group from a compound of the general Formula

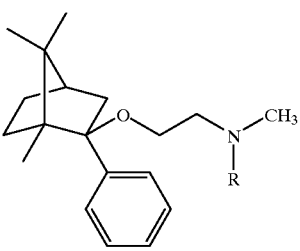

(wherein R is a protecting group);
and if desired splitting the racemic compound of the Formula I thus obtained into the optically active isomers and if desired converting the compound of the Formula I into a pharmaceutically acceptable acid addition salt or setting free the base from a salt.

According to process a.) demethylation may be preferably carried out by reacting the compound of Formula II with a compound of the general Formula

Hlg-COOR¹ (IV)

(wherein $R^1$ is alkyl or aryl and Hlg represents halogen) and treating the compound of the general Formula

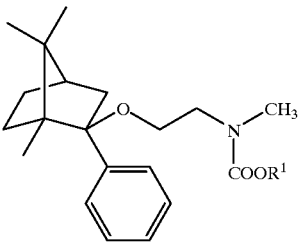

thus obtained (wherein $R^1$ is as stated above) with a base.

In the starting materials of the general Formula IV $R^1$ is preferably straight or branched chain lower alkyl having 1–4 carbon atoms or optionally substituted phenyl. It is preferred to use compounds of the general Formula IV wherein $R^1$ is methyl, ethyl or phenyl, particularly preferably ethyl chloro formate.

The reaction of the compound of the Formula II and the chloro formate of the general Formula IV may be carried out in an organic solvent. As reaction medium preferably aromatic hydrocarbons (e.g. benzene, toluene, xylene) may be used. The reaction may be performed under heating, preferably at a temperature between 80° C. and 110° C., particularly at 80–85° C. One may proceed preferably by using the halogeno formate of the general Formula IV—preferably the chloro formate—in a 2–4 molar excess. The reaction time is several hours, preferably 4–8 hours.

The reaction between the compounds of the Formulae II and IV results in the formation of a compound of the general Formula V (wherein $R^1$ is as stated above). The reaction having been completed one may work up the reaction mixture preferably by evaporating the reaction mixture and converting the compound of the general Formula V without isolation into the compound of the Formula I.

The compound of the general Formula V is treated with a base. For this purpose preferably alkali hydroxides (e.g. sodium hydroxide, or potassium hydroxide) may be used. The reaction is carried out in a solvent. As reaction medium aliphatic alkanols (e.g. methanol, ethanol, etc.) may be used. One may work preferably in ethanol as medium. The reaction is performed under heating, preferably under reflux. The reaction time is 10–20 hours.

The reaction mixture may be worked up in a manner known per se. One may proceed preferably by removing the precipitated inorganic salts by filtration, evaporating the solvent, dissolving the residue in an organic solvent (e.g. halogenated hydrocarbons e.g. dichloro ethane), extracting the organic solution with water, evaporating the aqueous extract and fractionating the residue in vacuo.

According to method b.) of the process of the present invention the protecting group is removed from a compound of the general Formula III. The protecting group R may be preferably optionally substituted benzyl, particularly benzyl.

The benzyl group may be removed by catalytic hydrogenation in a manner known per se. As catalyst preferably palladium or platinum may be applied, preferably in the form of palladium on charcoal. Hydrogenation may be carried out under heating, preferably at 40–80° C. Reduction may be performed under a pressure of 1–50 bar, preferably 5–10 bar. Hydrogenation may be carried out in a solvent, preferably in a lower alkanol, particularly in ethanol as medium.

The reaction mixture may be worked up in a manner known per se. One may proceed e.g. by filtering off the catalyst and evaporating the filtrate.

The racemic compound of the Formula I may be split into optically active isomers. Resolution may be carried out in a manner known per se. Thus one may proceed by reacting the racemate of the Formula I with an optically active acid, (e.g. optically active tartaric acid, di-toluoyl tartaric acid, campher sulfonic acid, etc.) separating the diastereomeric salts formed by fractionated crystallization and setting free the optically active base of the Formula I from the salt by treatment with a base (e.g. alkali hydroxide). Physical resolution (e.g. chiral column) is applicable as well.

The compound of the Formula I may be converted into a pharmaceutically acceptable acid addition salt by methods known per se. The compound of the Formula I may be reacted with the corresponding acid in a suitable solvent as medium, whereupon the salt is precipitated.

According to a preferred embodiment of the present invention (1R,2S,4R)-(-)-2-phenyl-2-methylaminoethoxy-1,7,7-trimethyl-bicyclo[2.2.1]heptane and pharmaceutically acceptable acid addition salts thereof may be prepared by a) demethylating (1R,2S,4R)-(-)-2-phenyl-2-dimethylaminoethoxy-1,7,7-trimethyl-bicyclo[2.2.1]heptane; or b) removing the benzyl group from (1R,2S,4R)-(-)-2-phenyl-2-benzylmethylaminoethoxy-1,7,7-trimethyl-bicyclo[2.2.1]heptane; or c) splitting racemic (1R,2S,4R)-(-)-2-phenyl-2-methylaminoethoxy-1,7,7-trimethyl-bicyclo[2.2.1]heptane of the Formula I into the optically active isomers;

and if desired converting (1R,2S,4R)-(-)-2-phenyl-2-methylaminoethoxy-1,7,7-trimethyl-bicyclo[2.2.1]heptane into a pharmaceutically acceptable acid addition salt thereof or setting free the base from a salt.

The starting material of the Formula II may be prepared as described in Hungarian patent specification No 179,164 or laid-open Hungarian patent application Ser. No 5997190 (T/60996).

The starting materials of the general Formula III may be prepared by reacting phenyl-borneol with an amine of the general Formula

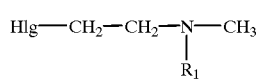

(VI)

(wherein $R^1$ is as stated above and Hlg represents halogen). Thus e.g. the starting material of the Formula III, wherein $R^1$ stands for benzyl, may be prepared by reacting phenyl borneol with benzyl-methylamino-ethyl chloride.

The compounds of the general Formula IV are commercially available or can be prepared by methods known per se.

The compound of the Formula I and pharmaceutically acceptable acid addition salts thereof exhibit valuable anxiolytic effect. The therapeutical effect can be demonstrated by the following tests.

The following compounds were used in the test systems:

(1R,2S,4R)-(−)-2-phenyl-2-methylaminoethoxy-1,7,7-trimethyl-bicyclo[2.2.1]heptane-fumarate (Compound A);

(1R,2S,4R)-(−)-2-phenyl-2-dimethylaminoethoxy-1,7,7-trimethyl-bicyclo[2.2.1]heptane-fumarate (Compound B).

The receptor profiles of the two compounds are remarkably different (Table II).

Among 5-HT receptors, Compound A binds only to 2C while Compound B is not selective at 2C. Moreover, the two compounds have different affinities to other receptor populations, for example Compound B shows significant binding at sigma receptors while Compound A does not.

There are clear differences in the anxiolytic profile of the two compounds, too. Compound A proved to be effective in the elevated plus maze test while, surprisingly, Compound B did not show any effect. Moreover, Compound B significantly antagonized the mCPP induced anxiety in a rat model where Compound A was completely ineffective up to 3.0 mg/kg i.p. (Table III). These differences were unpredictable.

Further differences were found in tests examining the sedato-hypnotic side effects of the compounds. Compound A inhibited the spontaneous motor activity in higher doses only and potentiated the hexobarbital induced narcosis to a lesser extent when compared to Compound B (Table IV).

Methods

Receptor binding assay

The different brain regions of 120–200 g male Wistar rats were used for receptor binding assays except for $5\text{-HT}_{2c}$ receptors where binding studies were performed on porcine choroid plexus. Protein content of the membrane fraction was determined as described by Lowry [Lowry, O. H., Rosebrough, M. J., Farr, A. L. and Randall, R. Y.: J. Biol. Chem., 193: 265–275, 1951]. The results are summarized in Table I.

TABLE I

| Receptor | Ligand | Brain area | NSB(conc.) | Reference |
|---|---|---|---|---|
| $5\text{-HT}_{1A}$ | $^3$H-8-OH-DPAT 0.7 nM | frontal cortex | 5-HT (10 μM) | Peroutka, S. J. J. Neurochem. 47:529 (1986). |
| $5\text{-HT}_{2A}$ | $^3$H-ketanserin 1.0 nM | frontal cortex | cyproheptadine (10 μM) | Leysen, J. E. et al.: Mol. Pharmacol. |

TABLE I-continued

| Receptor | Ligand | Brain area | NSB(conc.) | Reference |
|---|---|---|---|---|
| | | | | 21:301 (1982). |
| $5\text{-HT}_{2C}$ | $^3$H-mesulergin 1.0 nM | choroid plexus | mianserin (1 μM) | Pazos, A. et al. Eur. J. Pharmacol. 106: 539 (1984). |
| $D_1$ | $^3$H-SCH 23390 0.78 Nm | striatum | cis-flupentixol (1 μM) | Hietala J. et al., Neurosci. Lett 108: 289 (1990) |
| $D_2$ | $^3$H-spiperone 0.5 nM | striatum | butaclamol (1 μM) | Leff, S. et al., Eur. J. Pharmacol 70: 71 (1981). |
| Sigma | $^3$H-pentazocine 3.0 nM | cerebellum | haloperidol (10 μM) | Costa B. R. et al., Febs Lett., 251: 1,253 (1989). |

TABLE II

| Receptor | Compound B $K_i$ (nM) | Compound A $K_i$ (nM) |
|---|---|---|
| $5\text{-HT}_{1A}$ | >10,000 | >10,000 |
| $5\text{-HT}_{2A}$ | 35.0 | >100.0 |
| $5\text{-HT}_{2C}$ | 9.0 | 20.0 |
| $D_1$ | >1000.0 | 10,000 |
| $D_2$ | >100.0 | >100.0 |
| Sigma | 52.0 | >100.0 |

Elevated Plus-Maze

The elevated plus-maze consisted of two open and two 40 cm wall enclosed arms of the same size (50×15 cm) arranged in the shape of a cross. The arms of the same type were opposite to each other. The junction of the four arms forms a central square area (15×15 cm). The apparatus is made of wooden material elevated to a height of 50 cm from the floor and illuminated by a dim light from above.

Male Sprague-Dawley rats weighing 220–260 g were treated with the test or reference compounds 60 minutes prior to the test. They were then placed onto the central square area and were subjected to the test for 5 minutes. The following parameters were determined:

Time spent in the open arms;
Time spent in the closed arms;
Number of entries into the open arms;
Number of entries into the closed arms.

A compound was considered to be effective when significant increase was found either in the time spent in the open arms or in the number of entries into the open arms when compared to the control animals. Minimum Effective Doses (MED) were determined based on the times spent in the open arms for each compound examined (Table II) [Pelow et al., J. Neurosci. Methods, 14: 149–169, 1985].

mCPP Induced Anxiety

The tests were carried out on male Wistar rats weighing 160–220 g according to Kennett [Kennett, G. A., Whitton, P., Shah, K. and Curzon, G. Eur. J. Pharmacol., 164: 445–454, 1989.]. The animals were treated either with the test compound or with vehiculum (0.4% methyl cellulose solution). Twenty minutes later either mCPP (m-chlorophenyl-piperazin) or physiological saline was administered subcutaneously. The animals were kept in the dark for additional 20 minutes, then they were placed into the light-dark apparatus (Omnitech, Digiscan, Model RXYZCM16) and their motor activity was recorded for five minutes. The testbox consisted of one dark and one lit compartment of the same size (39×20×29 cm) with an 8×8 gate providing free passage for the animals between the two compartments. The lit area was illuminated by a 40 W red light bulb 30 cm above the floor. Motor activity was recorded as the number of interruptions of the infrared light beams (16 beams 2 cm and 16 beams 8 cm above the floor). The number of crossing in the lit compartment was considered as the measure of antagonistic effect on mCPP induced anxiety. Data were statistically analyzed by one way ANOVA followed by Dunnet's t-test. MED values for the two comnpounds are given in Table III.

TABLE III

| Anxiolytic tests | Compound B MED* (mg/kg) | Compound A MED (mg/kg) |
|---|---|---|
| Elevated plus maze | >10.0 | 1.0 |
| Inhibition of mCPP induced anxiety (i.p.) | 0.5 | >3.0 |

*=minimal effective dose

Inhibition of Spontaneous Motor Activity

Spontaneous motor activity was measured as described earlier [Borsy et al., Arch. Int. Pharmacodyn. 124: 1-, 1960.] in a 10 box apparatus (Dews) 3—3 mice in each compartment. Mice were treated either with test compounds or with vehiculum 60 minutes prior to the test. The number of interruptions of the infrared light beams was counted, $ID_{50}$ values were calculated by linear regression analysis (Table IV).

Potentiation of Hexobarbital Induced Narcosis

Male NMRI mice weighing 20–25 g were treated p.o. with the test compound or with vehiculum in 20 ml/kg volume 60 minutes prior to the iv. injection of 40 mg/kg (10 ml/kg) hexobarbital. The sleeping animals were placed on a flat surface lying on their left side and the accurate sleeping and awakening times were recorded. The animals were considered to be awaken when they rolled up from their side.

Sleeping times 2.5 times higher than the average of the control group were considered as criterion for potentiation (cut up method), results were expressed as percent increase compared to control values, $ED_{50}$ values were calculated from the dose response curves according to Litchfield-Wilcoxon. $ED_{50}$ values are shown in Table IV.

TABLE IV

| Test | Compound B $ED_{50}$ | Compound A $ED_{50}$ |
|---|---|---|
| Inhibition of spontaneous motor activity | 31.5 | 57.0 |
| Potentiation of hexobarbital induced narcosis | 0.5 | 4.0 |

In summary, the results presented here clearly show that Compound A significantly differs from Compound B as reference material both in receptor profile (mechanism of action), and in animal models of anxiety. These effects of the Compound A described herein are obviously distinct from those of Compound B and are surprising in view of the similarities between the two compounds.

According to the present invention there are provided pharmaceutical compositions comprising as active ingredient the compound of the Formula I or a pharmaceutically acceptable acid addition salt thereof. It is preferred to use as active ingredient (1R,2S,4R)-(−)-2-phenyl-2-methylaminoethoxy-1,7,7-trimethyl-bicyclo[2.2.1]heptane or a pharmaceutically acceptable acid addition salt— particularly the fumarate. thereof.

The pharmaceutical compositions according to the present invention may be suitable for oral (e.g. tablets, coated tablets, hard or soft gelatine capsules, solutions, suspensions, syrups); parenteral (e.g. subcutaneous, intramuscular or intravenous injections); rectal (e.g. suppositories) or nasal (e.g. spray, aerosol) administration. The active ingredient may be set free instantaneously whereby the period of action is determined by that of the active ingredient per se. Sustained release compositions may also be prepared in which case the period of action is also affected by the form and components of the pharmaceutical composition.

The pharmaceutical compositions of the present invention may be prepared by conventional methods of pharmaceutical industry.

The tablets or capsules may contain various types of lactose (monohydrate, anhydrous, dried), mannitol or cellulose (dried, microcrystalline) as filler. As binding agent e.g. gelatine, polyvinyl pyrrolidone (the molecular weight may be varied), various types of cellulose ethers (e.g. hydroxypropyl cellulose, hydroxypropyl methyl cellulose, ethyl cellulose, etc.), hydrolized starch, various vegetable gums (e.g. acacia gum, guar gum, etc.) may be used in solutions formed with water or $C_{1-4}$ aliphatic alcohols or mixtures thereof. As disintegrating agent e.g. various types of starch (potato, maize, wheat starch) and so called super-disintegrants, e.g. carboxymethyl cellulose (tradename Ac-di-sol), sodium carboxymethyl starch (Primojel, Ultraamilopektin, Explo-Tab), polyvinyl pyrrolidone (tradename Poliplasdone), etc. may be used. As sliding auxiliary agent e.g. alkaline earth metal stearates (e.g. magnesium stearate, calcium stearate), fatty acids (e.g. stearic acid), glycerides (e.g. tradename Precirol, Cutina H), paraffin oil, silicon oils, silicon oil emulsions, talc or silicic acid may be used.

Tabletting and encapsulation may be carried out by dry or wet granulation procedure or by simple powder homogenization.

Sustained release solid pharmaceutical compositions may be prepared by any suitable known method. Thus skeleton tablets may be produced by using as retardizing agent hydrophilic polymers (e.g. hydroxypropyl cellulose, hydroxypropyl methyl cellulose, carboxymethyl cellulose, polyacrylic acid derivatives), polysacharose (guar gum, xanthane gum) or mixtures thereof, or hydrophobic polymers (e.g. ethyl cellulose, methacrylic acid ester copolymers, polyvinyl acetate, polyvinyl butyral, etc. or mixtures thereof). Dissolution of the active ingredient may be retardized also by using a mixture of a hydrophilic and hydrophobic polymer or a mixture of a polymer and a fatty substance. Skeleton type tablets may also be prepared in the form of multi-layer tablets, whereby the active ingredients are embedded into different layers and by this method the dissolution profile may be better adjusted to the individual pharmacokinetical characteristics of the active ingredients.

The compound of the Formula I and pharmaceutically acceptable acid addition salts thereof may also be prepared as sustained release coated pellets. Such pellets may be prepared separately from each active ingredient or from a mixture of the active ingredients. Pellets may be prepared by means of extrusion spheronization, rotogranulation methods or by applying onto placebo pellets. The pellets may be coated in rotating or fluidization apparatus. As coating agent the solution of water-insoluble polymers in organic solvents (preferably $C_{1-3}$ aliphatic alcohols and/or $C_{1-2}$ polychlorinated hydrocarbons and/or acetone and/or ethyl acetate) or aqueous dispersions may be used.

The active ingredients of the present invention may also be finished in the form of osmotic or diffusion-osmotic compositions. Such compositions may be produced by preparing tablets which contain the active ingredient and hydrophilic polymers (e.g. hydroxypropyl methyl cellulose), coating said tablets with a film layer semipermeable (e.g. cellulose acetate) or permeable (e.g. aminomethacrylate copolymer) towards the active ingredient by methods known per se and boring a passageway into the layer through which the active ingredient can be osmotically pressed into the aqueous medium.

By suitable preparation of the sustained release compositions the setting free velocity of the active ingredient may be preferably adjusted to the rate that in vitro at least 80% of the active ingredient should be released within 2–24 hours (measured in accordance with the methods disclosed in the Pharmacopeia).

The dosage of the compound of the Formula I may vary between broad limits and is determined on a case-by-case basis under taking into consideration e.g. the condition and body weight of the patient, the seriousness of the disease, the route of administration, etc. The oral daily dose amounts generally to about 0.01–1.0 mg/kg, preferably 0.05–0.5 mg/kg.

Further details of the present invention are to be found in the Examples without limiting the scope of protection to said Examples.

EXAMPLE 1

Preparation of (1R,2S,4R)-(−)-2-phenyl-2-methylaminoethoxy-1,7,7-trimethyl-bicyclo[2.2.1]heptane To a solution of 57.14 g (0.19 mole) of (1R,2S,4R)-(−)-2-phenyl-2-dimethylaminoethoxy-1,7,7-trimethyl-bicyclo[2.2.1]heptane in 150 ml of anhydrous toluene 61.8 g (0.57 mole) of ethyl chloro formate are added dropwise at 80–85° C. within an hour and a half. The reaction mixture is heated at 80–85° C. for 6 hours, whereupon it is cooled to 20° C., washed with water, dried and evaporated.

The oily product thus obtained (58.5 g) is dissolved in 60 ml of ethanol, and the solution is added dropwise at 50° C. to a solution of 72.5 g (1.29 mole) of potassium hydroxide and 270 ml of 96% ethanol. The reaction mixture is refluxed for 20 hours. The precipitated product is filtered at 20° C. and the filtrate is evaporated. The residual oil is dissolved in 100 ml of dichloro ethane, the solution is extracted with water, dried and evaporated. The residue is fractionated in vacuo. Thus 27.09 g of the desired compound are obtained in the form of yellow oil, yield 49.6%, bp.: 130° C./25 Pa.

HNMR: NMR (CDCl$_3$).

δ0.60–0.80 [m, 1H, C(6)-H(ax)]; 0.88–0.90 [ss, 6H, 2×CH$_3$]; 1,17 [s, 3H, —CH$_3$]; 1.00–1.30 [m, 2H,C(5)-H(ax), C(6)-H(eq)]; 1.53 [s, 1H, —NH]; 1.6–1.70 [m, 1H, C(5)-H (eq)]; 1.86 [t, J=4.3, C(4)-H]; 2.00 [d, 1H, J=13.8, C(3)-H (ax)]; 2.25 [dt, 1H, J=13.3 J=3.9, C(3)-H(eq)]; 2.42 [s, 3H, —N—CH$_3$]; 2.50–2.75 [m, 2H, —N—CH$_2$—]; 2.80–2.90 [m, 1H —O—CH$_2$(1)]; 3.25–3.35 [m, 1H, —O—CH$_2$(2)-1]; 7.20–7.40[m, 4H, Ph—H]; 7.55 [d, 1H, J=7.5, Ph—H].

The fumaric acid salt is prepared by adding 11.5 g (0.04 mole) of (1R,2S,4R)-(−)-2-phenyl-2-methylaminoethoxy-1, 7,7-trimethyl-bicyclo[2.2.1]heptane to the boiling solution of 4.64 g (0.04 mole) of fumaric acid and 50 ml of anhydrous ethanol. The precipitated crystalline product is filtered, washed with ethanol and dried. The (1R,2S,4R)-(−)-2-phenyl-2-methylaminoethoxy-1,7,7-trimethyl-bicyclo [2.2.1]heptane-(E)-2-butenedioate (1/1) thus obtained melts at 178–180° C.

Analysis for the Formula: $C_{23}H_{33}NO_5$ (403.52)

|        | C      | H     | N      |
|--------|--------|-------|--------|
| calc.: | 68.46% | 8.24% | 3.47%; |
| found: | 68.15% | 8.08% | 3.52%. |

$[\alpha]_D^{20} = -45,4°$ (c = 0.4, DMSO).

EXAMPLE 2

Preparation of (1R,2S,4R)-(−)-2-phenyl-2-benzylmethylamino ethoxy-1,7,7-trimethyl-bicyclo[2.2.1]heptane 2.0 g (8.68 millimole) of (−)-phenyl-borneol are reacted in toluene at the boiling point with 0.53 g (11 millimoles) of 50% sodium hydride, whereupon a 46.16% toluene solution of a 3.9 g (9.8 millimoles) of benzylmethylaminoethyl chloride is added at the boiling point and the reaction mixture is refluxed for 3 hours. The reaction mixture is washed with water, dried and evaporated. The residual oil (3.7 g) is purified by column chromatography (eluent:hexane:ethyl acetate=10:1). Thus 2.6 g of the desired oily compound are obtained, yield 79.5%.

The oxalate (1/1) melts at 194–196° C. (from ethanol).
Analysis for the Formula: $C_{28}H_{37}NO_5$ (467.59)

|        | C      | H     | N      |
|--------|--------|-------|--------|
| calc:  | 71.92% | 7.98% | 2.99%; |
| found: | 72.08% | 7.83% | 3.08%. |

Preparation of (1R,2S,4R)-(−)-2-phenyl-2-methylaminoethoxy-1,7,7-trimethyl-bicyclo[2.2.1]heptane 0.4 g (1.06 millimole) of (1R,2S,4R)-(−)-2-phenyl-2-benzylmethylaminoethoxy-1,7,7-trimethyl-bicyclo[2.2.1] heptane is hydrogenated in ethanol in the presence of a 5% palladium-carbon catalyst at 60° C. under a pressure of 10 bar for 6 hours. The reaction mixture is filtered and the filtrate is evaporated. Thus in the form of a colourless oil 0.26 g of the desired compound is obtained, yield 85.2%. The fumaric acid salt is prepared as described in Example 1. The 2-(E)-butenedioate (1/1) melts at 179–180° C. ( from ethanol).

Analysis for the Formula: $C_{23}H_{33}NO_5$ (403.52)

|        | C      | H     | N      |
|--------|--------|-------|--------|
| calc:  | 68.46% | 8.24% | 3.47%; |
| found: | 68.50% | 8.18% | 3.42%. |

EXAMPLE 3

Preparation of Tablets 6 parts by weight of (1R,2S,4R)-(-)-2-phenyl-2-methylaminoethoxy-1,7,7-trimethyl-bicyclo[2.2.1]heptane-fumarate are admixed with 9 parts by weight of lactose and 3 parts by weight of microcrystalline cellulose. The powder mixture thus obtained is granulated with a solution of 0.5 part by weight of polyvinyl pyrrolidone and 4 parts by weight of ion exchanged water in a fluidization spraying granulating apparatus. To the dried granules 1.3 parts by weight of carboxymethyl cellulose and 0.2 part by weight of magnesium stearate are added and the granules are passed through a 1.00 mm sieve. The granules thus obtained are pressed on a rotating tabletting machine by using a dye (diameter 8 mm) into tablets with an average weight of 200 mg. Thus tablets weighing 200 mg and having an active ingredient content of 60 mg are obtained.

EXAMPLE 4

Preparation of Film Capsules

The granules prepared according to Example 3 are filled into hard gelatine capsules size No. 2.

EXAMPLE 5

Preparation of Sustained Release Tablets 10 parts by weight of (1R,2S,4R)-(-)-2-phenyl-2-methylaminoethoxy-1,1,7-trimethyl-bicyclo[2.2.1]heptane-fumarate, 9 parts by weight of hydroxypropyl methyl cellulose (Methocel K 4M, manufacturer Clorcon Ltd.) and 10 parts by weight lactose are admixed. The powder mixture is granulated with a solution of 0.4 part by weight of polyvinyl pyrrolidone and 4 parts by weight of isopropanol in a turbulent granulating apparatus. The granules are dried, whereupon 0.3 part by weight of talc and 0.3 part by weight of magnesium stearate are added. The granules are passed through a sieve (1.0 mm). The granules thus obtained are pressed into tablets weighing 300 mg and having an active ingredient content of 100 mg on a rotating tabletting machine by using a lentil formed dye (diameter 10 mm).

EXAMPLE 6

Preparation of Suppositories 7 parts by weight of (1R,2S,4R)-(-)-2-phenyl-2-methylaminoethoxy-1,7,7-trimethyl-bicyclo[2.2.1]heptane-fumarate are dispersed in 53 parts by weight of Witepsol S 58 suppository base melt at 50° C. The still liquid suspension is filled into suppository forms, solidified by cooling to 25° C. and the suppositories are removed from the forms. Thus suppositories weighing 6 g and having an active ingredient content of 20 mg are obtained.

What we claim is:

1. A method of anxiolytic treatment in a mammal, comprising:

administering to a mammal in need thereof, an effective amount of a compound having the formula

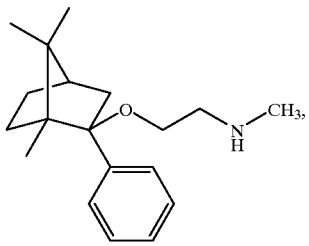

(I)

or one or more pharmaceutically acceptable acid addition salts thereof.

2. The method of anxiolytic treatment according to claim 1, wherein the effective amount of the compound of formula I obtains enhanced receptor selectivity.

3. A method of selectively binding 5-$HT_{2C}$ receptors in a mammal, comprising:

administering to a mammal in need thereof, an effective amount of a compound having the formula

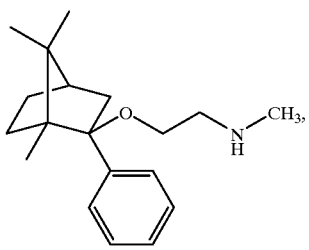

(I)

or one or more pharmaceutically acceptable acid addition salts thereof.

4. The method of selectively binding 5-$HT_{2C}$ receptors according to claim 3, wherein the selective binding takes place in the presence of both 5-$HT_{2B}$ and 5-$HT_{2C}$ receptors.

5. A method of anxiolytic treatment which avoids significant binding to sigma receptors, comprising:

administering to a mammal in need thereof, an effective amount of a compound having the formula

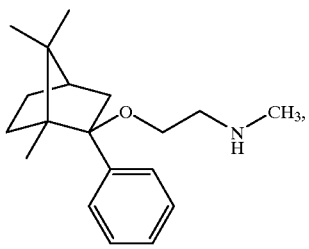

(I)

or one or more pharmaceutically acceptable acid addition salts thereof.

6. A method of anxiolytic treatment with reduced potentiation of hexobarbital-induced narcosis, comprising:

administering to a mammal in need thereof, an effective amount of a compound having the formula

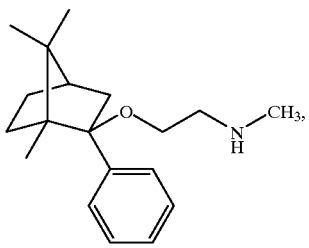

(I)

or one or more pharmaceutically acceptable acid addition salts thereof.

7. The method according to claim 1, wherein the compound according to formula I is at least one member selected from the group consisting of a racemic form and one or more optically active isomers.

8. The method according to claim 1, wherein the compound according to formula I is (1R,2S,4R)-(−)-2-phenyl-2-methylaminoethoxy-1,7,7-trimethyl-bicyclo[2.2.1]heptane, or one or more pharmaceutically acceptable acid addition salts thereof.

9. The method according to claim 1, wherein the pharmaceutically acceptable acid addition salts thereof are formed with the compound according to formula I and at least one member selected from the group consisting of organic acids and inorganic acids.

10. The method according to claim 1, wherein the pharmaceutically acceptable acid addition salts thereof are formed with the compound according to formula I and at least one member selected from the group consisting of hydrochloric acid, hydrogen bromide, sulfuric acid, nitric acid, phosphoric acid, acetic acid, propionic acid, malic acid, lactic acid, maleic acid, fumaric acid, tartaric acid, succinic acid, methanesulfonic acid, and p-toluenesulfonic acid.

11. The method according to claim 1, wherein the pharmaceutically acceptable acid addition salt is a fumarate of the compound according to formula I.

12. The method according to claim 1, wherein the compound is administered by at least one route selected from the group consisting of oral administration, parenteral administration, rectal administration, and nasal administration.

13. The method according to claim 12, wherein the compound is administered in combination with one or more pharmaceutically acceptable excipients.

14. A method of enhancing the anxiolytic effect of the compound according to the formula

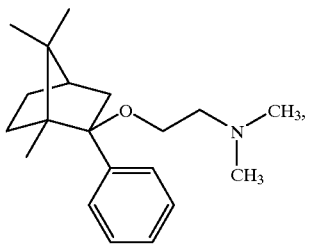

(II)

comprising:
    demethylating the compound of the formula (II) to obtain a compound according to the formula

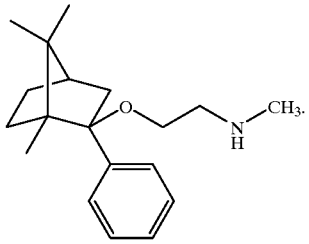

(I)

* * * * *